United States Patent [19]
Reich et al.

[11] Patent Number: 5,662,599
[45] Date of Patent: *Sep. 2, 1997

[54] DISPOSABLE WOUND DRESSING AND SUPPORT UNIT

[75] Inventors: Marshall P. Reich; Barry F. Shesol, both of Aurora, Colo.

[73] Assignee: No Mulligans, LLC, Aurora, Colo.

[*] Notice: The portion of the term of this patent subsequent to Nov. 15, 2013, has been disclaimed.

[21] Appl. No.: 603,466

[22] Filed: Feb. 20, 1996

[51] Int. Cl.⁶ .................................................. A61F 13/00
[52] U.S. Cl. .................................................. 602/79; 602/59
[58] Field of Search .................................. 602/41, 53, 75, 602/79; 606/213, 215, 216

[56] References Cited

U.S. PATENT DOCUMENTS

| | | | |
|---|---|---|---|
| 3,245,406 | 4/1966 | Chardack | 602/79 |
| 5,456,660 | 10/1995 | Reich et al. | 602/79 |

*Primary Examiner*—Richard J. Apley
*Assistant Examiner*—Kim M. Lee
*Attorney, Agent, or Firm*—Edwin H. Crabtree; Ramon L. Pizarro; Donald W. Margolis

[57] ABSTRACT

A disposable wound dressing and support unit for delivering a variety of standard gauze pads on top of a wound and providing for a painless access to the wound. The disposable wound dressing and support unit consists of an elongated bidirectional (stretches laterally) wrap which includes a window opening therethrough and disposed along the length of the wrap. The bidirectional wrap is adaptable for conforming to various parts of the anatomy of a patient and includes a releasable hook fastener at one end for securing the end to any portion of the wrap. The wrap is made of a loose weave material. The wound dressing and support unit may be received around the trunk, head, limb, hand and other parts of the anatomy. Also, one end of the wound dressing and support unit may be bifurcated for ease in receipt around various parts of the human anatomy. The window opening may be of different widths, lengths and geometric shapes for application to different sizes and types of wounds. A gauze pad is received over the window opening with the sides of the pad permanently secured to the sides of the window opening. The window in the wrap allows for visual inspection of the gauze pad relative to the nature of wound drainage, the amount of drainage, and when the disposable unit needs to be replaced. The window further allows for improved exchange of gases and liquids secreted from the wound and through the gauze pad.

15 Claims, 1 Drawing Sheet

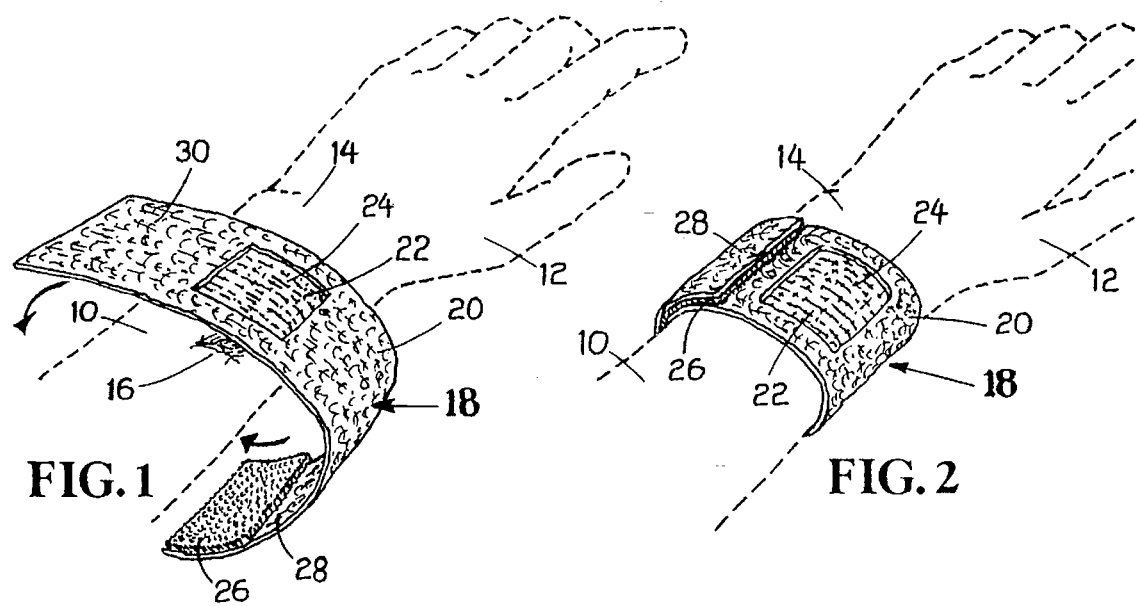
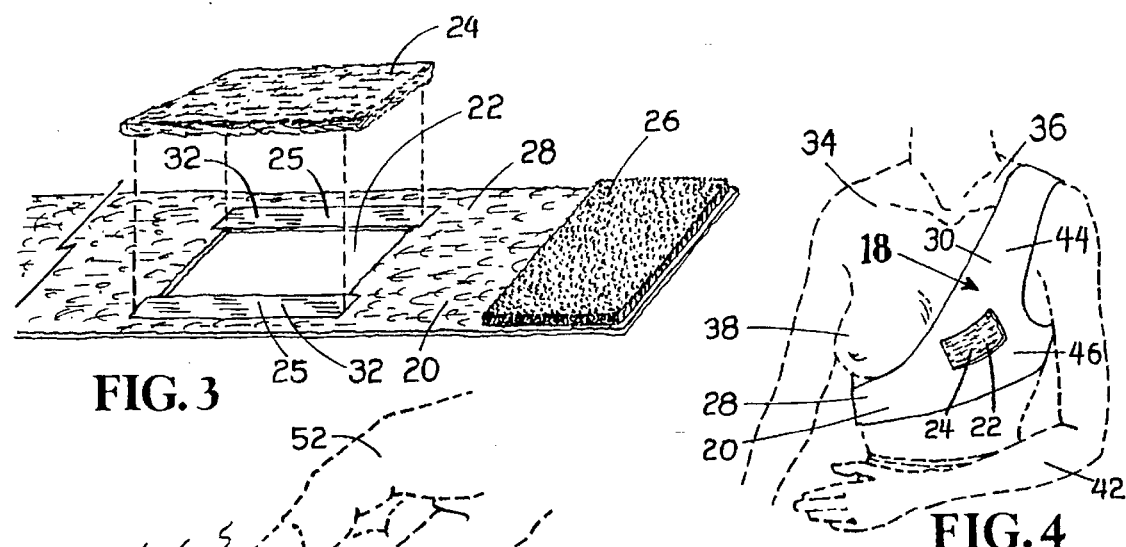
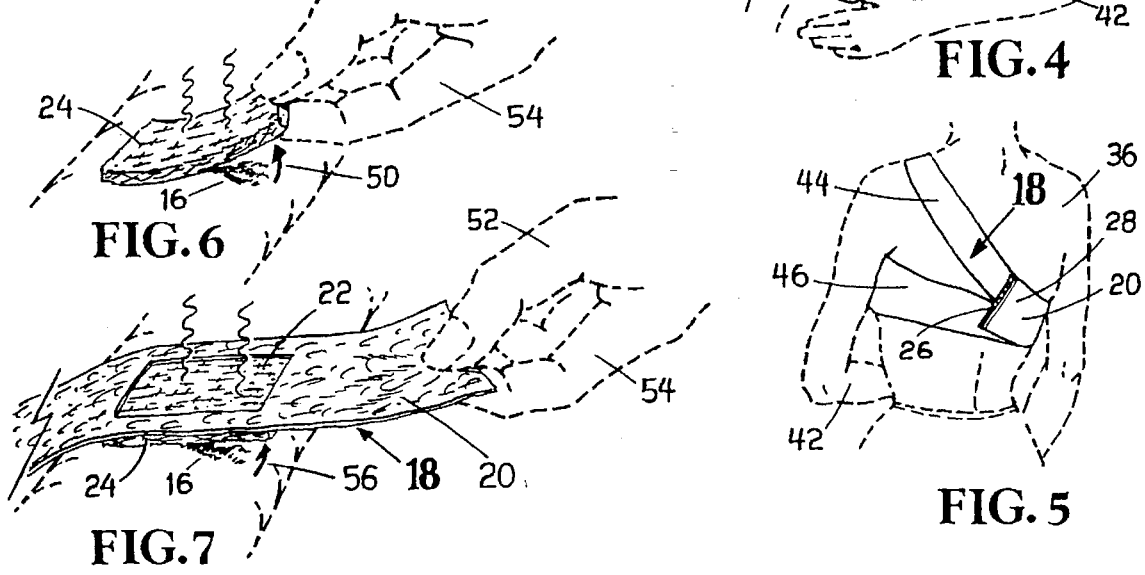

DISPOSABLE WOUND DRESSING AND SUPPORT UNIT

BACKGROUND OF THE INVENTION (a) Field of the Invention

This invention relates to wound dressings and wound bandages and more particularly, but not by way of limitation, to a disposable wound dressing and support unit having a wrap for holding a gauze pad or the like in place on top of a wound.

(b) Discussion of Prior Art

Because of the complexity of wound healing, the function of a wound dressing may be integral to the success of that process. Wound dressings function as:

a. a protective barrier from outside sources of irritation.

b. provide for mechanical support to the fragile wound surface.

c. serve to form an occlusive barrier to provide an optimal environment for certain wound types.

d. function to absorb wound byproducts that tend to accumulate and complicate healing.

e. act as an agent for wound debridement which acts to clean and prepare a wound bed for healing.

f. may have value as an acceptable camouflage for unsightly wound appearances.

The wound dressing is most often secured in place by the application of an adhesive to the skin. This seemingly simple and universal method of dressing fixation actually has limited applicability accompanied with a significant list of inadequacies, problems and patient dissatisfactions:

a. difficulty with conforming to some anatomic locations and contours, particularly in active body locations.

b. an increasing incidence of adhesive allergies resulting in blister formation, rashes, weeping wounds, scars, and permanent pigmentation problems.

c. inability to adhere in areas of raw, open wounds, or wounds with vulnerable scab formation.

d. lack of satisfactory adherence in hair bearing areas or areas of hypersensitivity.

e. pain associated with adhesive removal in hair bearing areas or areas of hypersensitivity.

f. adhesive system is not reusable when loosened by movement or moisture, thus necessitating reapplication.

g. lack of usefulness in wet to dry dressing situations. Due to the moist dressing, adhesives will not hold the dressings in place, making the wet to dry concept totally ineffective.

h. possibly the most important of issues is that a wound dressing, if not properly chosen, can significantly retard and limit wound healing.

i. adhesives used will stick to protective gloves now used by all handlers of wound products, often tearing the gloves and making them ineffective as a protective barrier.

The advent of AIDS and other serious infectious and contagious diseases has changed the thinking and application of traditional wound dressings. The matter of exposure apply to all parties involved in the care of a patient such as the health care provider administering the care, the patient and the individual removing the wound dressing. The subject invention addresses this acute problem.

Also, traditional wound dressings are applied with various tapes, elastic wraps or gauze wraps. These dressing wraps have intrinsic negative aspects as compared to the subject wound dressing and support unit described by virtue of:

a. restricted areas of usefulness in terms of adhesives. Adhesives also cannot easily be "readjusted".

b. wraps produce significant bulk of material and that bulk also reduces the gas exchanged from the wound surface.

c. wraps obscure the nature and quantity of wound drainage.

d. wraps require some dexterity and finesse by the patient, which at times is not possible or at least discourages the patient from getting involved in his or her own care. This may lead to other individuals having to assist or take over care which increases the expense.

e. wraps often require a secondary means of fixation which thereby complicates the dressing change process.

f. wraps lead to waste of materials or increased production of biohazardous materials.

Heretofore there have been a variety of different types of wound dressings using adhesives and stretchable wraps such as described in the following patents.

U.S. Pat. No. 4,732,146 to Fasline et al. discloses a surgical wound dressing device having a frame with an opening for receiving different types of wound dressings. A dressing is held in place by straps attached to one side of the frame with one end of the straps including releasable Velcro fasteners.

U.S. Pat. No. 4,917,112 to Kalt describes a bandage having an opening with the opening covered with a transparent membrane. The membrane is designed to allow air and vapors to permeate outward from the wound and prevent contaminants from entering in the opposite direction.

In U.S. Pat. No. 4,909,243 to Frank et al., a two piece wound dressing is shown having an adhesive layer on one side of a baseplate with an opening in the baseplate to expose the wound and the epithelium area around the wound. A second adhesive layer on one side of a wound pad secures a wound dressing above the opening in the baseplate.

U.S. Pat. No. 4,907,579 to Kum, U.S. Pat. No. 5,167,613 to Karami et al., and U.S. Pat. No. 3,779,242 to McCullough disclosed different types of adhesive bandages for providing open areas to wounds to enhance healing. In U.S. Pat. No. 5,036,838 to Sherman, a foam plastic orthopedic fabric is described having a Velcro tab at one end of the fabric.

In U.S. Pat. No. 4,470,410 to Elliott a stretchable sleeve is shown with Velcro fasteners at the ends of the sleeve. The sleeve includes a central opening with a releasable flap for retaining an intravenous tube or the like.

U.S. Pat. No. 4,709,695 to Kohn et al., U.S. Pat. No. 4,399,816 to Spangler, U.S. Pat. No. 5,086,763 to Hathman, and U.S. Pat. No. 4,926,883 to Strock all describe different types of wound surrounding dressings and bandages. Also U.S. Pat. No. 4,190,054 to Brennan and U.S. Pat. No. 4,658,811 to Beaird disclose stretchable bandages having loop and hook type attachment ends for encircling the head of a patient.

In U.S. Pat. No. 5,456,660 to the subject inventors, a wound dressing support device is described for holding a variety of standard gauze pads in place on top of an open wound. The device includes an elongated unidirectional wrap with a window opening therethrough. Around the sides of the window is a non-adhesive fastener for releasably engaging a portion of the sides of the gauze pad.

None of these prior art patents disclose the unique structure and advantages of the subject invention as described herein when addressing the need of a disposable wound dressing and support unit in combination.

SUMMARY OF THE INVENTION

In view of the foregoing, it is an object of the present invention to provide a disposable wound dressing and support unit which is easy to apply and holds a variety standard cotton gauze pads in place on top of a wound. The unit uses a bidirectional material which prevents slippage either up or down. However, the material allows readjustment by virtue of its unique closure system without adhesives.

Another object of the invention is to provide a disposable wound dressing and support unit that eliminates the need of adhesive tape which causes pain during removal, possible allergic reactions, and flimsy application due to hair, moisture and wound complications. Adhesives also do not allow for readjustment of tension for unlimited times.

Still another object of the subject wound dressing and support unit is the unit includes a window opening therethrough. The window is accessed over the top of the gauze pad and allows for visual inspection relative to the amount of drainage from the wound and affords an indication on when the disposable combination unit needs to be changed. The window opening provides a window for the gauze pad or dressing to breathe and allow gases and liquids secreted from the wound to evaporate thereby allowing for improved healing. Also of importance is the window allows examination of the nature of drainage without having to disturb the gauze pad, thus having positive benefits for the wound while at the same time reducing the chances of contamination to the patient and the health care provider. The simplicity of use of the invention reduces nursing care time, subsequent exposure time to the wound from contaminants and allows the patient to assume more of his or her own care, thereby influencing reduced hospital stay time and the need for reliance on other individuals.

Yet another object of the wound dressing and support unit is that the bidirectional wrap is provided with hook fasteners at one end for engaging a portion of loop like material of the wrap allowing for easy adjustment in either loosing or tightening the wrap when the gauze pad is received over the wound. The unit is designed so that there is no excess material or use of supplies, thus keeping down the cost of health care. Also, decreased bulk of materials means less biohazardous wound materials and consequently less cost of removal of these materials.

A further object of the invention is that the unit is lightweight, nonconstricting, versatile and able to be applied by a single individual. By the nature of using a wrap with a gauze pad attached thereto, the disposable unit can be removed and replaced from infectious and contagious wounds at a safe distance from the wound. Also, the wrap provides improved leverage for ease in removing the gauze pad when compared to removing a pad by hand. Further, the wrap is bidirectional and therefore stretchable laterally along its length for versatility in conforming to different parts of the anatomy of the trunk, the hand, the head and the limbs.

In summation, the subject invention eliminates the deficiencies of other prior art dressing systems while offering the following objects and advantages that support, simplify, and promote wound healing. They are:

a. a disposable, sterile, lightweight and non-allergenic wound care unit.

b. ease in application and removal by the patient and at a distance from the wound, not requiring, in most instances, the use of more than one hand.

c. adaptable to different anatomic locations and wound sizes.

d. allows visualization of the wound and/or dressing.

e. improves evaporation of gases and fluids from the wound surface to the dressing.

f. promotes reduced pressure to the wound bed by the nature of the dressing window.

g. preserves the integrity of the skin by avoiding adhesives and abrasive materials.

h. allows frequent dressing changes with minimal disruption to the wound bed or local tissues.

i. acts as a combination wound dressing and dressing support, all as one unit.

j. improves patient compliance by nature of its simplicity and ease.

k. reduces chances of contamination and exposure to health care providers.

l. acts as a brace to support the wound and its surrounding tissues.

m. reduces biohazardous materials and cost of their removal.

The subject disposable wound dressing and support unit provides for delivering a variety of standard gauze pads on top of a wound and providing for a painless access to the wound. The disposable wound dressing and support unit consists of an elongated bidirectional (stretches laterally) wrap which includes a window opening therethrough and disposed along the length of the wrap. The bidirectional wrap is adaptable for conforming to various parts of the anatomy of a patient and includes a releasable hook fastener at one end for securing the end to any portion of the wrap. The wrap is made of a loose weave material. The wound dressing and support unit may be received around the trunk, head, limb, hand and other parts of the anatomy. Also, one end of the wound dressing and support unit may be bifurcated for ease in receipt around various parts of the human anatomy. The window opening may be of different widths, lengths and geometric shapes for application to different sizes and types of wounds. A gauze pad is received over the window opening with the sides of the pad permanently secured to the sides of the window opening. The window in the wrap allows for visual inspection of the gauze pad relative to the nature of wound drainage, the amount of drainage, and when the disposable unit needs to be replaced. The window further allows for improved exchange of gases and liquids secreted from the wound and through the gauze pad. Further, other types of wound dressing materials may be used equally well for attachment to the sides of the window.

These and other objects of the present invention will become apparent to those familiar with medical dressings and problems related to the healing of wounds and sores from the following detailed description, showing novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a perspective view of a conventional cotton gauze pad permanently secured to the sides of a window disposed along the length of an elongated wrap. The gauze pad is positioned for receipt on top of a wound in the forearm of a patient.

FIG. 2 is a similar perspective view as shown in FIG. 1 with the window opening and gauze pad in place over the wound and the wound dressing and support unit secured around the forearm.

FIG. 3 is a rear view of a portion of the wound dressing and support unit with one end having hook fasteners. The window opening is shown being angular in shape with a gauze pad positioned for bonding to sides of the window.

FIG. 4 and 5 illustrate perspective views of the wound dressing and support unit with the gauze pad and window received over a breast of a female patient. One end of the wrap is bifurcated for ease in receipt over the top of a shoulder and underneath an arm of the patient. The divided end is secured to the other end of the wrap at the back of the patient.

FIG. 6 is a side view of a standard gauze pad being removed from an infectious wound using a finger and a thumb next to the wound.

FIG. 7 is a side view of a gauze pad bonded as a unit to the subject wound dressing and support unit and being removed from the same infectious wound as shown in FIG. 6 using a finger and thumb but at a safe distance from the wound.

DESCRIPTION OF THE PREFERRED EMBODIMENTS

In FIG. 1, a perspective view of a human forearm 10 with hand 12 is shown. In this view a top 14 of the forearm 10 has an open wound 16. The subject disposable wound dressing and support unit is designated by general reference numeral 18. The unit 18 includes an elongated wrap 20 having different lengths and widths depending on the application. The wrap 20 has a window opening 22 therethrough and disposed along it's length. A standard gauze pad 24 is secured to sides 25 of the window opening 22 as shown in FIG. 3. The pad 24 may be a 2×2, 2×4, 4×4, 8×8 inch pad or any other desired dimension for receipt around the window opening 22 and having sufficient size to cover the wound being treated. Also, while the window opening 22 is shown having a rectangular shape in the drawings, it may have various geometric configurations and sizes for ease in conforming to the type of wound being treated on the body. The wrap 20 is bidirectional along it's length for stretching the wrap 20 when it is applied around a portion of the body or limb. The width of the wrap 20 is not expandable or stretchable for preventing the distortion of the window opening 22 when in use. The wrap's length may vary from 6 inches to 4 feet and greater. The wrap's width may vary from 1½ inches to 12 inches and greater. The wrap 20, for example, is made of a stretch bonded laminate developed and manufactured by Kimberly-Clark Corporation. The wrap 20 includes a loose loop-like weave on the front and back surfaces of the wrap for engaging hook fasteners 26 mounted at the end of a first end portion 28 of the wrap 20. An important feature of the invention is the use of the hook fasteners 26 to engage the loose loop-like weave of the wrap 20 along any portion of it's length. This feature makes the wound dressing and support unit 18 infinitely adjustable along the length of the wrap 20 for ease in tightening or loosening the unit 18.

In FIG. 2 the gauze pad 24 and window are received on top of the wound 16. A second end portion 30 of the wrap 20 is wrapped around the forearm 10 and the hook fasteners 26 releasably secured to the loop-like weave of a portion of the wrap 20. While only one pad 24 is shown in the drawings, it can be appreciated that depending on the type of wound and it's characteristics, one or more pads 24 can be placed one on top of each other. As mentioned above, the window opening 22 provides a quick visual means for a doctor or patient to determine when the gauze pad 24 along with the disposable wound dressing and support unit 18 as a unit needs to be replaced. Also, because the pad 24 has a loose "loop like" woven structure, the pad 24 with window opening 22 allows the wound 16 to breathe easily thereby allowing a free flow of liquids and gases to escape to the atmosphere for enhanced wound debridement.

In FIG. 3, a rear view of a portion of the wound dressing and support unit 18 is shown with the first end portion 28 having the hook fasteners 26 and the wrap 20 having an angular window opening 22. In this view, the cotton gauze pad 24 is disposed above the window opening 22 and positioned for permanent attachment to sides 25 of the opening 22. The pad 24 may be secured using an adhesive 32, heating bonding, or any other securing agent to hold the pad 24 to the sides 25 of the window opening 22 and on top of the wound being treated.

In FIG. 4, a front perspective view of an upper portion 34 of a female human body 36 wherein the disposable unit 18 is used for treating a wound on a women's left breast. In this example, the pad 24 and window opening 22 are placed over the wound in the left breast with the first end portion 28 of the wrap 20 placed beneath or over a right breast 38 and around a portion of the women's waist. The second end portion 30 of the wrap 20 is bifurcated for ease in securing the unit 18 over a shoulder 40 and beneath a left arm 42. The second end portion 30 when divided includes an upper portion 44 received over the shoulder 40 and a lower portion 46 received under the left arm 42.

In FIG. 5 a rear perspective view of the female human body 36 is shown with ends 48 of the upper portion and lower portion 44 and 46 of the bifurcated second end portion 30 engaged by the hook fasteners 26 of the first end portion 28 of the wrap 20. Obviously, by the use of the hook fasteners 26, the wrap 20 can be quickly adjusted by tightened or loosened on the human body 36. The use of the bifurcated second end portion of the wrap 20 is but one example of the flexibility of the unit 18 for being contoured for wounds on various parts of the human anatomy.

In FIG. 6 a side view of a gauze pad 24 being removed from an infectious wound 16. Note the sharp angle, represented by arrow 50, required to lift the gauze pad 24. Also, note a finger 52 and a thumb 54 used to lift the gauze pad 24 are disposed next to the wound presenting a safety concern for a patent or care giver changing the dressing.

In FIG. 7 a side view of the subject wound dressing and support unit 18 is shown removing the gauze pad 24 secured to the wrap 20 from the infectious wound 16 as shown in FIG. 6. Note in this view, a lower angle, represented by arrow 56, is required to remove the pad 24 due to the leverage provided by the length of the wrap 20. By the nature of an elongated wrap 20, the pad 24 can be removed more gently because of the improved leverage. Also, the gauze pad 24 can be removed at a distance of 6 inches and greater from the wound 16 for improved safety to the person changing the dressing. While not shown in the drawings, the wrap 20 can be gripped using both hands at first and second end portions 28 and 30 when removing and replacing the gauze pad 24 on top of an open wound.

While the invention has been particularly shown, described and illustrated in detail with reference to the preferred embodiments and modifications thereof, it should be understood by those skilled in the art that changes in form and detail may be made therein without departing from spirit and scope of the invention as claimed except as precluded by the prior art.

The embodiments of the invention for which an exclusive privilege and property right is claimed are defined as follows:

1. A disposable wound dressing and support unit for holding a gauze pad in place on top of a wound and providing for painless access to the wound, the unit adaptable for conforming to various parts of the anatomy of a patient, the unit comprising:

an elongated wrap having a top and a bottom, said wrap having a window opening therethrough, said window opening adapted for receipt above and on top of the gauze pad disposed on top of the wound;

fastener means disposed on the bottom of said wrap and along a side of said window opening for permanently engaging a portion of the gauze pad; and securing means attached to a first end portion of said wrap for engaging a portion of said wrap at any desired location along its length and securing said wrap on the patient.

2. The unit as described in claim 1 wherein said wrap is an elastic bidirectional wrap stretchable in two directions along a length of said wrap.

3. The unit as described in claim 2 wherein said elastic bidirectional wrap includes a loose weave material on the front and back surface said wrap.

4. The unit as described in claim 3 wherein said securing means is a hook fastener attached to the first end portion of said wrap, said hook fastener releasably engaging the loose weave material of said wrap.

5. A disposable wound dressing and support unit for holding a gauze pad in place on top of a wound and providing for painless access to the wound, the unit adaptable for conforming to various parts of the anatomy of a patient, the unit comprising:

an elongated wrap having a top and a bottom, said wrap having a window opening therethrough, said window opening having different sizes and geometric configurations, said window opening adapted for receipt on top of the gauze pad disposed on top of the wound, said wrap made of an elastic bidirectional material for expansion along a length of said wrap;

fastener means disposed on the bottom of said wrap and along the sides of said window opening for permanently engaging a portion of pad the gauze pads; and securing means attached to a first portion end of said wrap for engaging a portion of said wrap at any desired location along its length and securing said wrap on the patient.

6. The unit as described in claim 5 wherein said securing means is a hook fastener attached to the first end of said wrap, said hook fastener releasable engaging a portion of said wrap along its length.

7. The unit as described in claim 5 wherein said wrap has a length in a range of 6 inches to 4 feet, said length of wrap allowing the gauze pad to be removed from an infectious wound at a safe distance of 1 to 4 feet.

8. The unit as described in claim 5 wherein said wrap has a width in a range of 1½ inches to 12 inches.

9. The unit as described in claim 5 wherein said wrap includes a second end portion which is bifurcated into a divided upper portion and a divided lower portion, said second end portion used for receipt around different extremities of the human body.

10. A method of using a disposable wound dressing and support unit for holding a gauze pad in place on top of a wound on an anatomy of a patient and providing for painless access to the wound, the unit adaptable for conforming to various parts of the anatomy of a patient, the steps comprising:

placing the gauze pad on top of the wound, the gauze pad permanently attached to a side of a window in an elongated wrap, said window disposed along a length of said wrap;

wrapping a first end portion and a second end portion of said wrap around part of the anatomy of the patient; and securing an end of said first end portion along a length of a portion of said second end portion.

11. The method as described in claim 10 further including the step of tightening and loosing said wrap by removing the end of said first end portion from the length of said second end portion and moving the end of the first end portion up and down the length of the second end portion and securing the first end portion thereto.

12. The method as described in claim 10 further including the step of removing said wound dressing and support unit by releasing said first end portion from said second end portion of said wrap and lifting the gauze pad from the wound using the first end portion of said wrap.

13. The method as described in claim 10 further including the step of removing said wound dressing and support unit by releasing said first end portion from said second end portion of said wrap and lifting the gauze pad from the wound using the second end portion of said wrap.

14. The method as described in claim 10 further including the step of removing said wound dressing and support unit by releasing said first end portion from said second end portion of said wrap and lifting the gauze pad from the wound using both the first and the second end portions of said wrap.

15. The method as described in claim 10 wherein said end of said first end portion includes hook fasteners for releasably securing the end of said first end portion along a length of a portion of said second end portion, the length of said wrap having a loose weave for releasably engagement with said hook fasteners.

* * * * *